Dec. 7, 1965 E. S. BOERNER Plant Pat. 2,578
ROSE PLANT
Filed Sept. 18, 1964
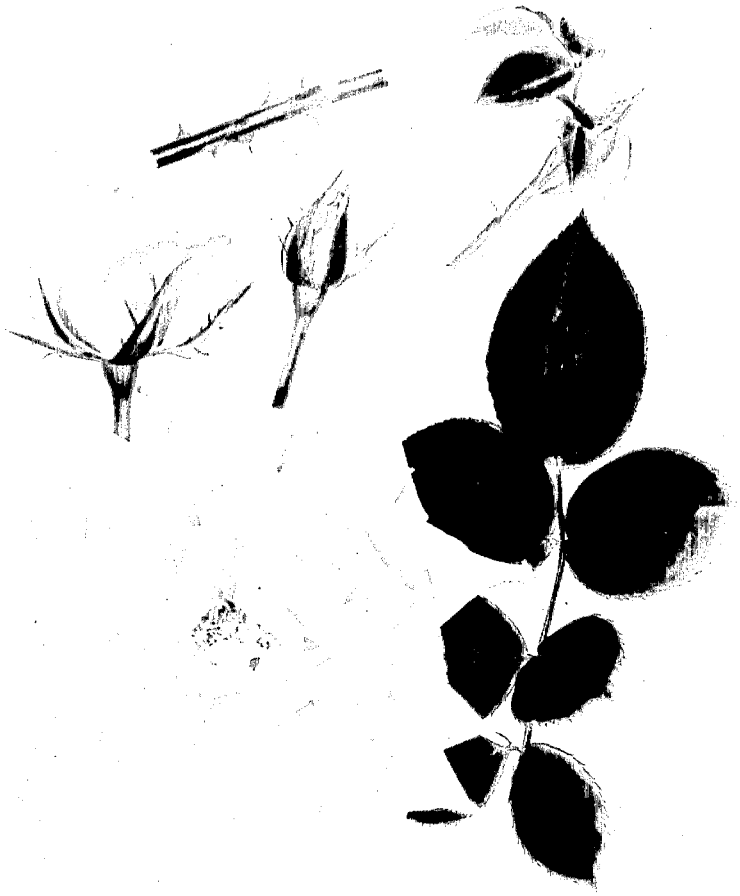
Inventor.
E. S. Boerner
By: Robb & Robb
Attorneys.

United States Patent Office

Plant Pat. 2,578
Patented Dec. 7, 1965

2,578
ROSE PLANT

Eugene S. Boerner, Newark, N.Y., assignor to Jackson & Perkins Company, Newark, N.Y., a corporation of New York Filed Sept. 18, 1964, Ser. No. 397,666
1 Claim. (Cl. Plt.—18)

The present invention relates to a new and distinct variety of rose plant of the hybrid tea class, which was originated by me by crossing two unnamed and unpatented seedlings of the rose variety known as "Golden Masterpiece" (Plant Patent No. 1,284).

The primary object of this breeding was to produce a new rose variety which bears flowers of pink color while at the same time maintaining the large flower size of the yellow flowers of "Golden Masterpiece." This objective was fully achieved along with other desirable improvements, as evidenced by the following unique combination of characteristics which are outstanding in the new variety and which distinguish it from its parents, as well as from all other varieties of which I am aware:

(1) A vigorous plant habit;

(2) A habit of bearing many more blooms per plant than plants of "Golden Masterpiece";

(3) A large flower size;

(4) A flower shape similar to that of the variety "Golden Masterpiece"; and (5) A distinctive and attractive general color tonality of the flowers, with the inside of the flower petals corresponding to Eosine Pink, lightly overcast with La France Pink, and the outside of the petals corresponding to Thulite Pink, lightly overcast with Cameo Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Golden Masterpiece" seedling.

*Pollen parent.*—"Golden Masterpiece" seedling.

Classification:

*Botanic.*—Hybrid tea.

*Commercial.*—Hybrid tea.

*Flower*

(Observations made from specimen grown outdoors at Newark, New York, in the early morning during the latter part of the month of September.)

Blooming habit: Recurrent—continuous.

Bud:

*Size.*—Large.

*Form.*—Ovoid; is not affected by wet or hot weather.

*Color.*—When sepals first divide—Eugenia Red, Plate 13. When petals begin to unfurl—Rose Red, Plate 12, very lightly overcast with Pomegranate Purple, Plate 12. When half brown: inside of petal—Rose Red, Plate 12, very lightly overcast with Tyrian Rose, Plate 12; reverse of petals—Scarlet-Red, Plate 1, lightly overcast with Tyrian Rose, Plate 12 in the center of the petal.

*Sepals.*—Slightly branched; curl back when petals begin to unfurl. Color: inside—Kildare Green, Plate 31; outside—Light Bice Green, Plate 17.

*Calyx.*—Color—Light Bice Green, Plate 17. Shape—funnel. Size—small. Aspect—smooth. Odor when rubbed—none.

*Peduncle.* — Length — medium. Aspect — rough. Strength—erect; slender. Color—Lettuce Green, Plate 5.

*Opening.*—Opens up well; is not affected by adverse weather conditions.

Bloom:

*Size.*—Large. Average size when fully expanded—5½ inches.

*Borne.*—Singly; many blooms per plant.

*Stems.*—Medium length; strong.

*Form (when first open).*—High centered. Permanence—retains its form to the end.

*Petalage.*—Double (full but open center). Number of petals under normal conditions—from 35 to 40.

*Color.*—Center of flower—Eosine Pink, Plate 1, very lightly overcast with La France Pink, Plate 1. Outer petals—Thulite Pink, Plate 26, very lightly overcast with Eosine Pink, Plate 1 on the outer edge of the petal. Base of petals (aiglet)—Light Chalcedony Yellow, Plate 17. Inside of petals—Eosine Pink, Plate 1, lightly overcast with La France Pink, Plate 1. Reverse of petals—Thulite Pink, Plate 26, lightly overcast with Cameo Pink, Plate 26. General tonality from a distance — Eosine Pink, Plate 1, lightly overcast with La France Pink, Plate 1.

*Discoloration.*—General tonality at end of first day—Eosine Pink, Plate 1, very lightly overcast with La France Pink, Plate 1. Second day—Eosine Pink, Plate 1, very lightly overcast with La France Pink, Plate 1. Third day—Eosine Pink, Plate 1, lightly overcast with La France Pink, Plate 1.

Petals:

*Texture.*—Thick; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; large.

*Persistence.*—Drop off cleanly.

*Fragrance.*—Slight. Nature—tea (average hybrid tea scent).

*Lasting quality.*—On the plant—long. As cut flower—long.

*Genital organs*

Stamens, anthers: Medium size; many; regularly arranged around styles. Color—Deep Chrome, Plate 3.

Stamens, filaments (threads): Medium length. Color—Cream Color, Plate 16.

Pollen: Color—Light Buff, Plate 15.

Styles: Bunched; uneven length; medium length; thin.

Stigmas: Color—Naples Yellow, Plate 16.

Ovaries: All enclosed in calyx.

Hips: None.

Seeds: None.

Form: Bush.

Growth: Vigorous; upright.

Foliage: Compound of 5 to 7 leaflets.

*Size.*—Medium.

*Quantity.*—Normal.

*Color.*—New foliage: upper side—Chromium Green, Plate 32, with serrations Carmine, Plate 1; under side—Rainette Green, Plate 31, with outer edge of leaf lightly overcast with Eugenia Red, Plate 13. Old foliage: upper side—Forest Green, Plate 17; under side—Varley's Green, Plate 18.

*Shape.*—Oval.

*Texture.*—Upper side—leathery. Under side—smooth.

*Ribs and veins.*—Ordinary.

*Edge.*—Serrated (sawtoothed).

*Serration.*—Both double and single; small.

*Leaf stem.*—Color—Yellowish Oil Green, Plate 5. Under side—prickly.

*Stipules.*—Medium length; slightly serrated.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: on main stalks from base—ordinary; on laterals from stalks—ordinary. Form—flat base; medium length; some hooked downward and some hooked upward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous plant habit, a habit of bearing many more blooms per plant than plants of "Golden Masterpiece," a large flower size, a flower shape similar to that of the variety "Golden Masterpiece," and a distinctive and attractive general color tonality of the flowers, with the inside of the flower petals corresponding to Eosine Pink, lightly overcast with La France Pink, and the outside of the petals corresponding to Thulite Pink, lightly overcast with Cameo Pink.

No references cited.

ABRAHAM G. STONE, *Primary Examiner.*